US012790643B2

(12) United States Patent
Brenneis et al.

(10) Patent No.: US 12,790,643 B2
(45) Date of Patent: Nov. 10, 2026

(54) METHOD, COMPUTER PROGRAM PRODUCT AND SYSTEM FOR SEQUENCING A PREPARED DNA STRAND AND A SENSOR UNIT

(71) Applicant: Robert Bosch GmbH, Stuttgart (DE)

(72) Inventors: Andreas Brenneis, Renningen (DE); Felix Michael Stuerner, Ulm (DE); Jochen Hoffmann, Renningen (DE); Nadezda Fomina, Redwood City, CA (US); Robert Roelver, Calw-Stammheim (DE); Tino Fuchs, Tuebingen (DE); Christian Grumaz, Waiblingen (DE)

(73) Assignee: Robert Bosch GmbH, Stuttgart (DE)

( * ) Notice: Subject to any disclaimer, the term of this patent is extended or adjusted under 35 U.S.C. 154(b) by 1072 days.

(21) Appl. No.: 17/960,490

(22) Filed: Oct. 5, 2022

(65) Prior Publication Data

US 2023/0151419 A1 May 18, 2023

(30) Foreign Application Priority Data

Nov. 16, 2021 (DE) ..................... 10 2021 212 841.6

(51) Int. Cl.

| | |
|---|---|
| ***G01N 33/48*** | (2006.01) |
| ***C12Q 1/6869*** | (2018.01) |
| ***G01N 21/64*** | (2006.01) |
| *C12Q 1/6806* | (2018.01) |

(52) U.S. Cl.
CPC ....... *C12Q 1/6869* (2013.01); *G01N 21/6428* (2013.01); *G01N 21/645* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 2011/0120890 A1 | 5/2011 | Macpherson et al. | |
| 2012/0264617 A1 | 10/2012 | Pettit | |
| 2019/0256905 A1 | 8/2019 | Jawaharlal et al. | |
| 2020/0096493 A1 | 3/2020 | Roorda et al. | |
| 2021/0047682 A1 | 2/2021 | Mendonsa et al. | |
| 2023/0340589 A1* | 10/2023 | Braganca .............. | B01L 3/5085 |

FOREIGN PATENT DOCUMENTS

WO 2019/173743 A1 9/2019

OTHER PUBLICATIONS

Köklü, Selma Öna, Ismail Yarici, and Yavuz Öztürk. "Investigation of Single Stranded DNA-Magnetic Nanoparticle Interaction by Magneto-Optical Linear Dichroism." Electrica 17.1 (2017): 3087-3091.*

Ding et al., "Single-Molecule Mechanical Identification and Sequencing: Proof of Principle," Nat Methods, Dec. 21, 2012 (2012), pp. 367-372.

* cited by examiner

*Primary Examiner* — Anna Skibinsky
(74) *Attorney, Agent, or Firm* — Maginot, Moore & Beck LLP

(57) ABSTRACT

A method of sequencing a prepared DNA strand includes providing the prepared DNA strand with nucleotides of the types dATP, dCTP, dGTP and/or dTTP, wherein at least one of the types of the nucleotides comprises a predetermined magnetic label. The method further includes placing the prepared DNA strand within a measuring range of a sensor unit comprising an operatively connected magneto-optical transducer unit and an optical sensor and optically exciting the magneto-optical transducer unit. The method continues with acquiring at least one value indicative of a fluorescence signal of the magneto-optical transducer unit, and assigning the acquired value to the at least one type of the nucleotides comprising the predetermined magnetic label.

13 Claims, 7 Drawing Sheets

METHOD, COMPUTER PROGRAM PRODUCT AND SYSTEM FOR SEQUENCING A PREPARED DNA STRAND AND A SENSOR UNIT

This application claims priority under 35 U.S.C. § 119 to patent application no. 10 2021 212 841.6 filed on Nov. 16, 2021 in Germany, the disclosure of which is incorporated herein by reference in its entirety.

The present disclosure relates to a method for sequencing a prepared DNA strand. The present disclosure also relates to a computer program product and system for sequencing a prepared DNA strand and a sensor unit for such a system.

BACKGROUND

The sequencing of nucleic acids such as DNA and RNA is of great importance in research and in the medical field. Several methods for sequencing nucleic acids are known. This includes third generation sequencing methods, which can be used to sequence a single nucleic acid molecule. This involves the use of nucleotides having different fluorescence labeling, for example, which are optically detected in real time as they are incorporated into a complementary nucleic acid strand. Another variant of third generation sequencing is nanopore sequencing, in which the nucleic acid is passed through a nanopore and the nucleotides are sequentially identified based on changes in the ionic current through the pore.

A sensor device for ion channel recordings, in which the sensor element comprises a diamond thin film substrate comprising a pore as the ion channel, is known from US 2011/0120890 A1. The sensor device can be used, among other things, for single molecule detection of DNA or for determining the ionic current through the pores and thus nanopore sequencing.

The use of charge transfer doped nanomaterials such as hydrogen-terminated diamond, nanotubes, nanowires or similar nanostructures to create a pH sensor or ion-sensitive sensor that directly detects the addition of a newly incorporated nucleotide when performing DNA sequencing by synthesis is known from US 2012/0264617 A1.

The use of a nanochannel in combination with at least one magnetic sensor to detect molecules labeled with magnetic nanoparticles is known from US 2021/0047682 A1. The molecules are identified via an output signal from the magnetic sensor. The molecules can be nucleotides of a DNA or RNA strand.

The use of a color center embedded near the surface in a substrate to detect a binding of a protein to a highly specific capture reagent located near the color center on the surface of the substrate is known from WO 2019/173743 A1. The binding of the protein changes the behavior of the color center and the change is read out, for example optically.

There is a need to provide other methods for sequencing nucleic acids.

SUMMARY

The object of the present disclosure is achieved by a method for sequencing a prepared DNA strand, comprising the steps:

- providing the prepared DNA strand with nucleotides of the types dATP, dCTP, dGTP and/or dTTP, wherein at least one of the types of the nucleotides comprises a predetermined magnetic label,
- placing the prepared DNA strand within the measuring range of a sensor unit comprising an operatively connected magneto-optical transducer unit and an optical sensor,
- optically exciting the magneto-optical transducer unit,
- acquiring at least one value indicative of a fluorescence signal of the magneto-optical transducer unit, and
- assigning the acquired value to the at least one type of the nucleotides comprising the predetermined magnetic label.

The method is used to sequence a prepared DNA strand, i.e., determine a nucleotide sequence of the prepared DNA strand. In the method, the sequencing of the prepared DNA strand is not carried out as it is being synthesized, but after it has been synthesized. The prepared DNA strand is therefore synthesized beforehand using an original nucleic acid strand to be examined. The original nucleic acid strand to be examined can be a DNA strand or an RNA strand. The synthesis of the prepared DNA strand is used for the incorporation of nucleotide-specific magnetic labels, wherein at least one of the types of nucleotides dATP, dCTP, dGTP and/or dTTP used for the synthesis comprises the predetermined magnetic label. The nucleotides dATP, dCTP, dGTP and/or dTTP can respectively be the native forms of the nucleotides or suitable derivatives thereof, i.e., modified variants thereof.

The synthesis of the prepared DNA strand derived from the original DNA strand or the original RNA strand is carried out using known molecular biological DNA synthesis methods, such as primer extension or polymerase chain reaction (PCR). Isothermal amplification methods, such as nucleic acid sequence-based amplification (NASBA), recombinase polymerase amplification (RPA), strand displacement amplification (MDA), replication by rolling circle (RCA), helicase-dependent amplification (HDA), or whole genome amplification (WGA), can be also used as DNA synthesis methods. The prepared DNA strand can thus be a DNA strand that is complementary to the original nucleic acid strand or a DNA copy of the original nucleic acid strand.

The magnetic label is specific to a particular type of nucleotide, so that the magnetic label can be used to deduce whether the nucleotide incorporated in a particular position in the prepared DNA strand is dATP, dCTP, dGTP or dTTP. This is the basis for identifying the nucleotides in the prepared DNA strand.

The measuring range of the sensor unit is defined such that differences between different magnetic labels and/or a single magnetic label are aligned with a measurement accuracy of the sensor unit, i.e., can be detected.

The sensor unit comprises a magneto-optical transducer unit that converts the magnetic fields of the magnetic labels or the magnetic field changes caused by the magnetic labels into optical signals, e.g., into optical signals having wavelengths in the visible range. A conversion into IR or ultraviolet wavelength ranges can also be provided.

The magneto-optical transducer unit comprises a solid body. The solid body can be a diamond solid body, for example deposited by means of chemical vapor deposition (CVD).

The solid body is doped with at least one color center. Color centers are point defects in otherwise nearly ideal transparent crystalline insulators or semiconductors with large band gaps such as diamond, silicon carbide or silicon dioxide. The color center can be a substitution defect in which an atom in the crystal has been replaced by an atom of a different type. The color center can be a void defect in which an atom is missing. The color center can also be a combination of a substitution defect and a void defect.

The solid body is doped near the surface with the at least one color center.

The state of the color center is then optically excited, e.g., by means of laser light.

Subsequently, at least one value indicative of a fluorescence signal of the magneto-optical transducer unit is acquired. To do this, the fluorescence signal of the magneto-optical transducer unit is detected with the optical sensor. Acquiring and evaluating the fluorescence signal enables a single measurement, for example indicative of a drop in the intensity of the fluorescence, to be carried out.

Since the fluorescence signal of the magneto-optical transducer unit corresponds to the magnetic field strength, or changes thereto, and these values can be assigned to the magnetic label, these values can be assigned to the types of the nucleotides of the prepared DNA strand. The types of the nucleotides of the prepared DNA strand are thus identified. The prepared DNA strand remains intact during the identification of the types of the nucleotides of the prepared DNA strand.

The solid body of the magneto-optical transducer unit doped with the at least one color center enables a spatially resolved detection of the fluorescence signal. The spatial resolution makes it possible to determine the sequence of the types of the nucleotides in the prepared DNA strand. Identifying the types of the nucleotides of the prepared DNA strand, together with determining their sequence, is equivalent to sequencing the prepared DNA strand.

Thus, by using a magneto-optical transducer unit, a method can be provided that has sufficient measurement accuracy to detect the changes in the magnetic field strength caused by the magnetic labels in a spatially resolved manner and so to enable sequencing of a prepared DNA strand.

The steps of identifying the types of the nucleotides of the prepared DNA strand and determining their sequence can be carried out in parallel, such as is the case when the nucleotides are identified sequentially along the prepared DNA strand. In that case, the sequence of the types of the nucleotides is determined at the same time. The determination of the sequence of the types of the nucleotides can also be carried out after the identification of the types of the nucleotides.

According to one embodiment, in a further step, the magneto-optical transducer unit is subjected to microwave radiation. The microwave radiation can be provided by an external microwave source. Alternatively, the microwave radiation can also be provided by molecules of the magnetic label. Irradiation with microwave radiation of variable frequency enables the fluorescence signal to be detected and evaluated as a function of the frequency of the microwave radiation. The fluorescence signal shows optically detectable magnetic resonances (ODMR; ODMR is optical detection of magnetic resonance), the frequency position of which is determined from the local magnetic field at the location of the color center via the Zeeman effect. In the case of a single NV center in diamond, two of these resonances occur; one below and one above the zero-field splitting frequency at approximately 2.87 GHz. The frequency spacing between these two resonances is indicative of the magnetic field strength, or change thereto, and in particular does not depend on the temperature of the diamond. This makes it particularly easy to evaluate the measurement results.

According to another embodiment, in further steps, the magneto-optical transducer unit is subjected to a static magnetic field and the magneto-optical transducer unit is subjected to an RF magnetic field.

The static magnetic field causes the spins of the magnetic label to precess, whereas the RF magnetic field is used to achieve phase alignment. This can increase the signal strength.

According to another embodiment, a gradient magnetic field is used as the static magnetic field. The gradient magnetic field makes it possible to achieve additional spatial resolution or spatial encoding. The gradient magnetic field can be provided by an electromagnet or by a permanent magnet. To achieve a 2-dimensional spatial resolution or spatial encoding, a carrier comprising the prepared DNA strand can be rotated 90° around the vertical axis.

Alternatively, the sensor unit can be rotated instead of the carrier. This makes it possible to simplify the evaluation of the measurement results and at the same time carry out a flat scan.

According to another embodiment, a spin polarization is carried out in a further step. A polarization of nuclear spins of the color center of the magneto-optical transducer unit can consequently be achieved. This allows the signal strength to be increased. Strong magnetic fields can be used to achieve a polarization of spins of the color center or an excitation of hyperfine transitions.

According to another embodiment, the sensor unit is stationary and the prepared DNA strand is shifted in a predetermined manner relative to the sensor unit, or the prepared DNA strand is stationary and the sensor unit is shifted in a predetermined manner relative to the prepared DNA strand, or the prepared DNA strand and the sensor unit are both shifted in a predetermined manner. For example, the prepared DNA strand can be moved past the sensor unit through a substrate of the sensor unit comprising micro-channels. The substrate of the sensor unit can be a MEMS (micro-electro-mechanical system) component. Alternatively, it is also possible for the prepared DNA strand to be stationary and to use an atomic/scanning force microscope (AFM), for example, at the measuring tip of which the sensor unit or components of the sensor unit are disposed.

The present disclosure further includes a computer program product configured to execute such a method, a system for sequencing a prepared DNA strand and a sensor unit for such a system.

BRIEF DESCRIPTION OF THE DRAWINGS

The present disclosure will now be explained with reference to the figures. The figures show.

DETAILED DESCRIPTION

Figure 1:
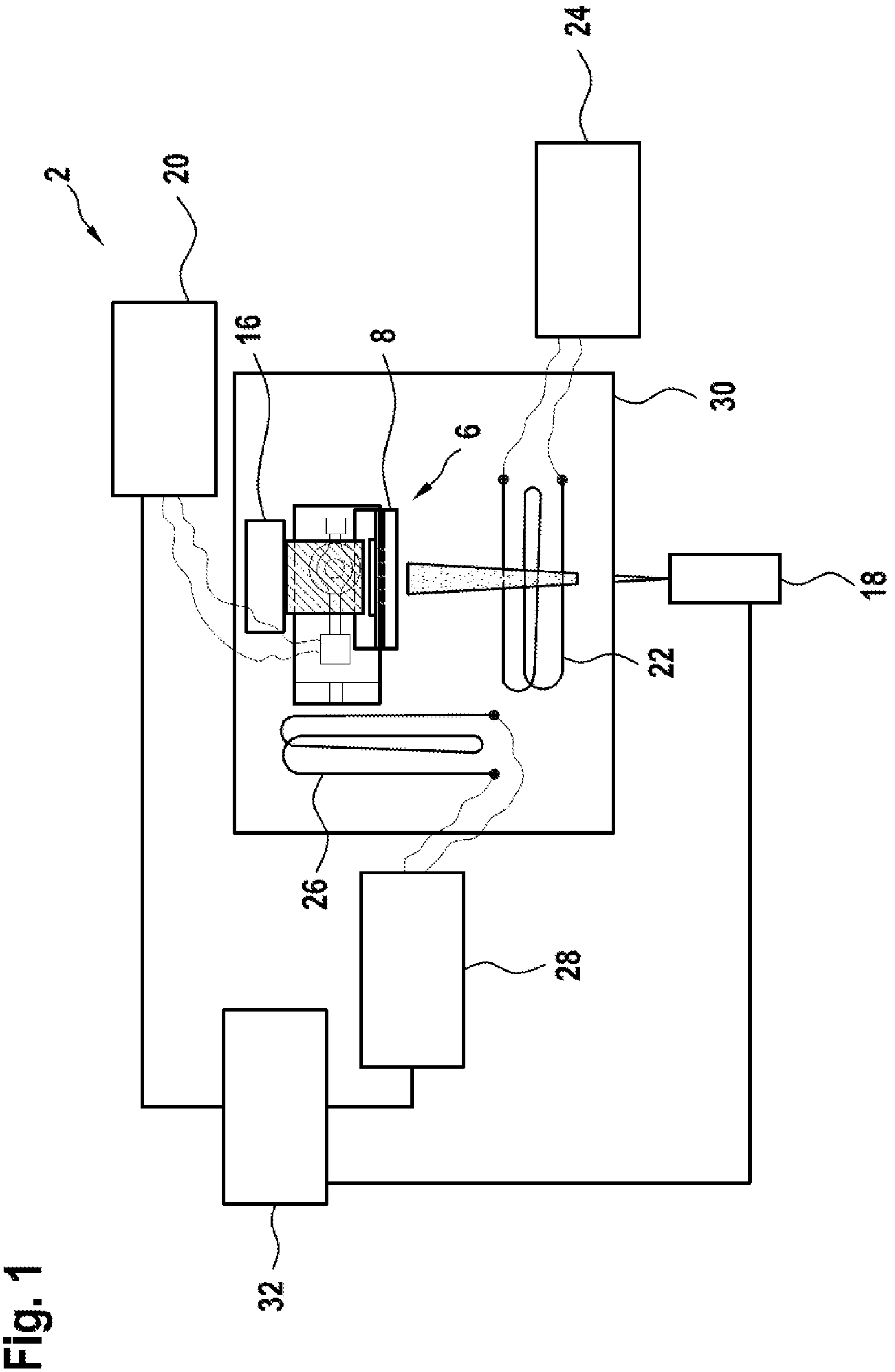
FIG. 1 a schematic illustration of components of a system for sequencing a prepared DNA strand.
Figure 2:
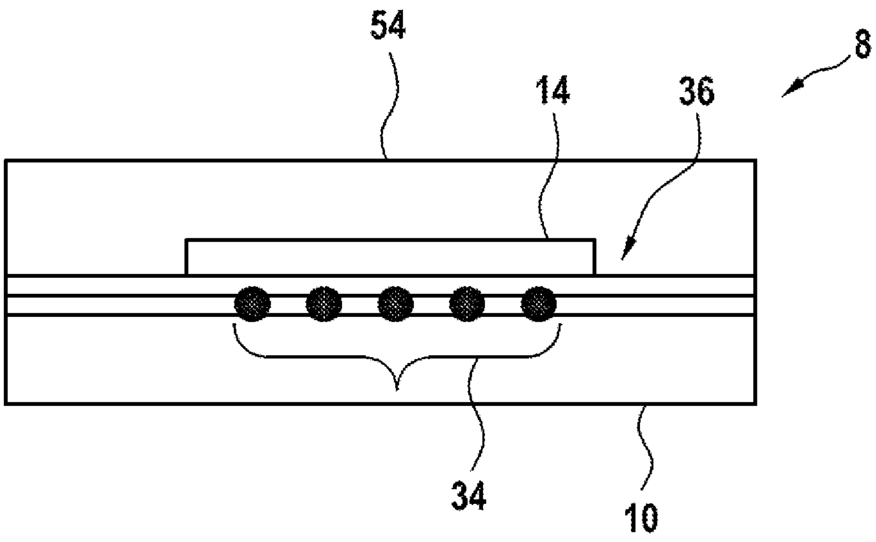
FIG. 2 a schematic illustration of a sectional view of a sensor unit of the system shown in FIG. 1.
Figure 3:
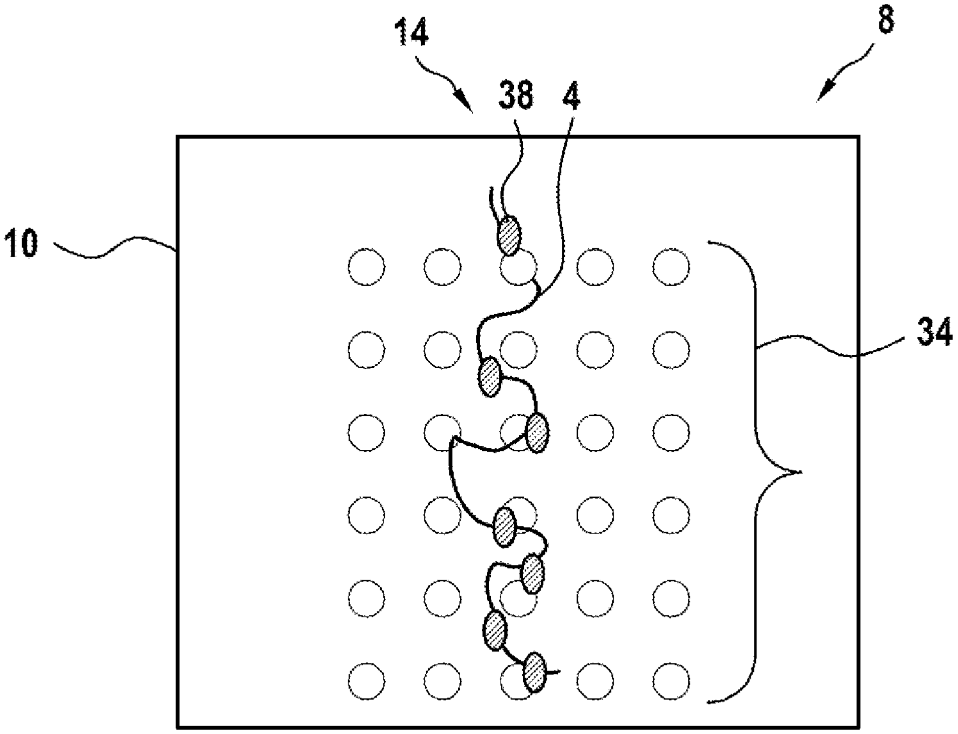
FIG. 3 a schematic illustration of a plan view onto the sensor unit shown in FIG. 1.

FIGS. 1 to 3 will be discussed first.

The figures show components of a system 2 for sequencing a prepared DNA strand 4 (see FIG. 3).

The components shown in FIG. 1 are a sensor unit 6, an optical sensor 16, a light source 18, a microwave and RF source 20, a DC solenoid 22 and a DC magnetic field source 24 which is connected to said DC solenoid in an energy-transferring manner, an AC solenoid 26 and an AC magnetic field source 28 which is connected to said AC solenoid in an energy-transferring manner, a magnetic shield 30 and a timing controller 32 for controlling said components.

On the input side, the sensor unit 6 comprises a magneto-optical transducer unit 8 for converting a magnetic input variable into an optical intermediate variable. For this purpose, the magneto-optical transducer unit 8 in the present design example comprises a base body 10 made of carbon in the form of diamond, which was deposited by means of CVD.

Furthermore, in the present design example, carbon having a minimized proportion of C13 is used.

The base body 10 was also specifically doped with color centers 34. In the present design example, nitrogen was used to dope the diamond. Therefore, in the present design example, the base body 10 is a diamond comprising NV color centers that can be disposed in a layer in the range of 5 nm to 100 nm below a measurement surface 36 of the base body 10. In the present design example, the color centers 34 are disposed in a range of 5 nm to 20 nm below the measurement surface 36 of the base body 10. In the present design example, the color centers 34 are furthermore disposed in the form of a rectangular grid in multiple rows and columns. The distance between the color centers 34 can be in a range of 1 nm to 20 nm. The distance between the color centers 34 allows the fluorescence signals of individual color centers 34 to be detected separately from one another. In the present design example, the distance between the color centers 34 is 4 nm. The diamond was homogeneously doped for this purpose.

The NV color centers, also known as NV centers (nitrogen-vacancy centers), are negatively charged nitrogen-vacancy centers. An NV color center is a defect in the pure carbon lattice of a diamond, in which a carbon atom has been replaced by a nitrogen atom and in which a directly adjacent carbon atom is missing in the diamond lattice (vacancy). Two different NV centers having different charge states are known. The term "NV color center" as used here refers to the negatively charged NV center. Negatively charged NV centers in diamond are highly sensitive magnetic field sensors that, unlike many other color centers, can be used at room temperature.

The base body 10 can alternatively be silicon carbide having silicon vacancies as color centers 34, for example, or germanosilicate glass having germanium-caused defects as color centers 34.

Furthermore, in the present design example, the base body 10 together with a component element 54 forms a microchannel 14, also referred to as a microfluidic channel, through which the prepared DNA strand 4 is passed. The microchannel 14 in the present design example was produced using a combination of MEMS techniques, such as anisotropic wet chemical etching, or dry etching, such as physicochemical etching, as well as wafer bonding or also gluing. The microchannel 14 can be configured in a transparent glass or plastic element glued onto the surface of the base body 10. The prepared DNA strand 4 can be passed through the microchannel 14 in a linear fashion in a known manner.

In the present design example, the light source 18 is a laser with which in particular the color centers 34 can be optically excited, while the AC magnetic field coil 26 is used to apply an alternating magnetic field to the color centers 34, so as to generate a fluorescence signal of the magneto-optical transducer unit 8, which is indicative of a magnetic label 38 of the prepared DNA strand 4. In the present design example, the light source emits green laser light in the wavelength range of 510 nm to 550 nm.

The microwave and RF source 20 comprising a coupling structure can be used to subject the color centers 34 to microwave radiation, for example having a variable frequency, in order to be able to obtain a frequency-dependent fluorescence signal. The microwave and RF source 20 can also be used to determine the location of magnetic resonances and couple in RF signals for nuclear spin hyperpolarization.

The fluorescence signal is then detected with local resolution by the optical sensor 16, e.g., a CCD detector, and then evaluated. In the present design example, a CCD camera is used as the CCD detector. The objective of the evaluation is primarily to determine at which locations and at which distances on the measurement surface of the base body 10 a magnetic activity of a magnetically labeled nucleotide can be detected. The position of the fluorescence signal within the prepared DNA strand 4 can be determined via the spatially resolved detection of the fluorescence signal from each individual color center 34.

In the present design example, the fluorescence signals of multiple color centers 34 are acquired at the same time. Multiple nucleotides of the prepared DNA strand 4 can thus be identified simultaneously in terms of their type. To identify the type of the nucleotides, each individual color center 34 is evaluated separately. In the present design example, the steps of identifying the types of the nucleotides of the prepared DNA strand 4 and determining their sequence are carried out in parallel. The two steps can alternatively be carried out one after the other. To identify further nucleotides of the prepared DNA strand 4, the prepared DNA strand 4 is shifted in the microchannel 14 in a predetermined manner relative to the sensor unit 6.

Depending on the length of the prepared DNA strand 4 and the number and arrangement of the color centers 34, it can alternatively also be possible to identify all of the nucleotides of the prepared DNA strand 4 at the same time in terms of their type. In this case, there is no need to shift the prepared DNA strand 4, so that the sensor unit 6 and the prepared DNA strand 4 can then both be stationary. For this purpose, the prepared DNA strand 4 can be fixed on the base body 10 in dry form, for example, so that a substantially planar arrangement is present.

The DC magnetic field source 24, for example consisting of a superconductor, can be used to subject the color centers 34 to a static magnetic field to cause a precession of spins of the magnetic label, while the microwave and RF source 20 can be used to achieve phase alignment in order to increase the signal strength of the fluorescence signal.

The AC magnetic field source 28 can be used to provide a driving magnetic field, the frequency of which corresponds to the Larmor frequency of the nuclear spins of the magnetic labels 38. In the present design example, the AC magnetic field source 28 provides a magnetic field that is disposed at a 90° angle to the magnetic field provided by the DC magnetic field source 24.

The system 2 is furthermore configured to carry out a spin polarization in order to further increase the signal strength of the fluorescence signal, as will be explained in more detail later.

The magnetic shield 30, e.g., made of μ-metal, in particular shields the prepared DNA strand 4, the sensor unit 6, the DC solenoid 22 and the AC solenoid 26 from external, interfering magnetic fields, which increases the measurement accuracy.

The timing controller 32 can be used to control said components to fulfill the abovementioned functions and/or tasks. For this purpose, the timing controller 32, and also the other mentioned components, can comprise accordingly configured hardware and/or software components.

Figure 4:
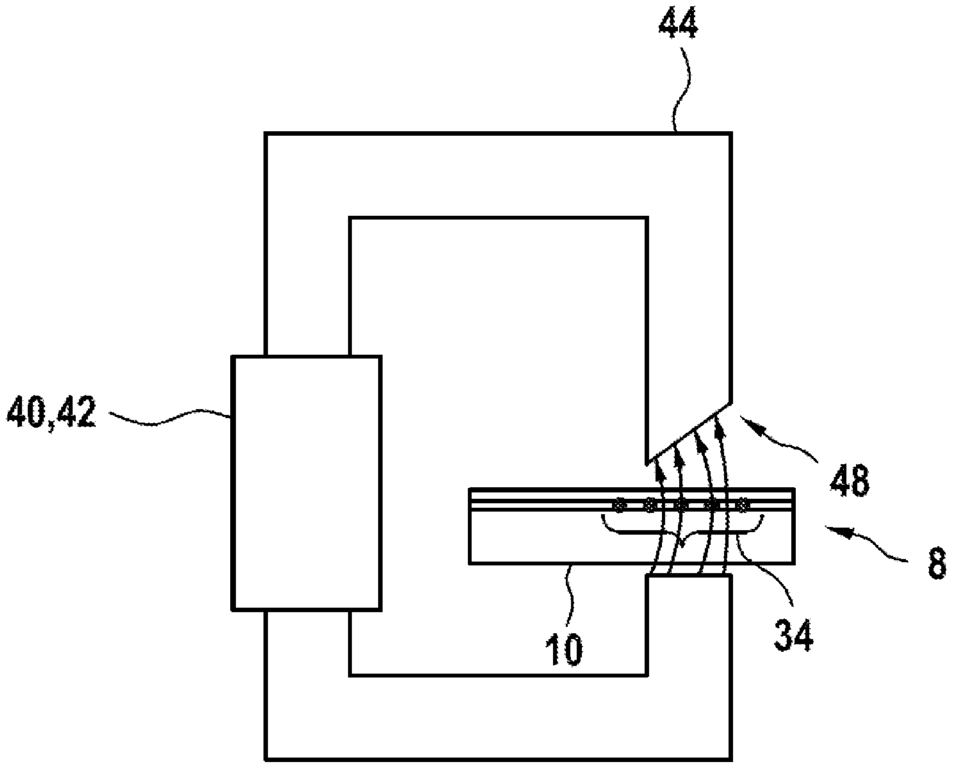
FIG. 4 a schematic illustration of an arrangement for providing a magnetic field having a predetermined field strength profile.

FIG. 4 will now be discussed as well.

The figure shows an arrangement for providing a gradient magnetic field.

The arrangement includes a permanent magnet 40 or electromagnet 42, which is connected to a yoke 44 made of a soft-magnetic material. The magneto-optical transducer unit 8 is disposed in an air gap 46.

In the present design example, yoke 44 has a phase 48 in the region of the air gap 46, so that the field strength of the magnetic field provided by the permanent magnet 40 or electromagnet 42 differs as a function of the position. In other words, each portion of the microchannel 14 is subjected to a different field strength of the magnetic field.

The gradient magnetic field encodes a spatial resolution. This occurs because a Zeeman splitting (i.e., the resonance frequency) of the color centers 34 is proportional to a static magnetic field. Thus, at least in one dimension, a resonance frequency is assigned to each location. The spatial resolution can be used to deduce the position of a detected magnetic label 38. The nucleic acid sequence of the prepared DNA strand 4 can be deduced from the spatial location of the magnetic label 38. The one-dimensional encoding can be extended to the second orthogonal direction in the plane by either rotating the sample 90 degrees, rotating the arrangement providing the gradient magnetic field 90 degrees relative to the sample, or, if the gradient magnetic field is generated by an electromagnet 42, a second comparable arrangement that generates a correspondingly 90° rotated gradient magnetic field can alternately be energized.

Figure 5:
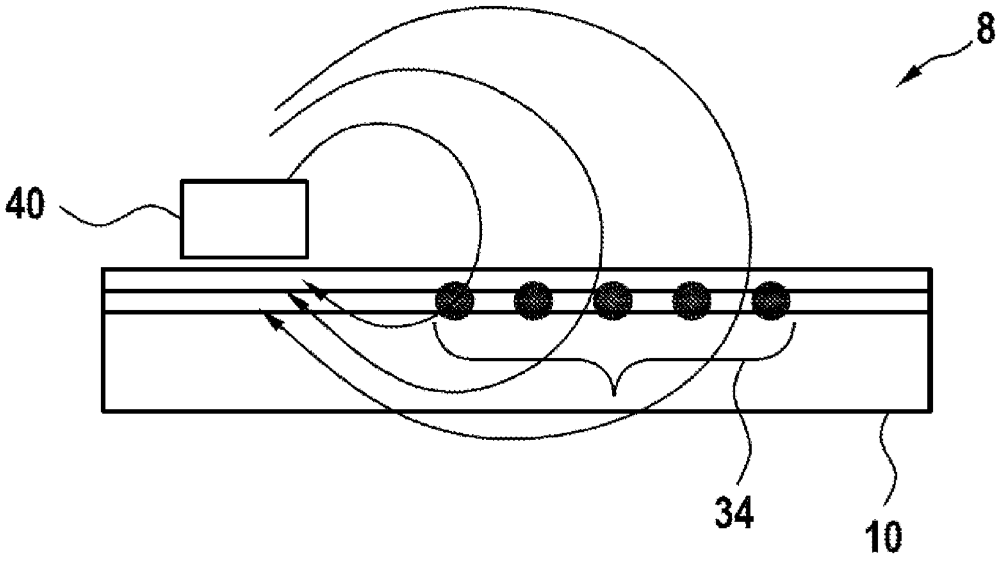
FIG. 5 a schematic illustration of a further arrangement for providing a magnetic field having a predetermined field strength profile.

FIG. 5 will now be discussed as well.

The figure shows another arrangement for providing a gradient magnetic field.

The arrangement comprises the permanent magnet 40, which is disposed on the base body 10. The permanent magnet 40 could have been deposited on the base body 10 by means of additive techniques, such as galvanic deposition.

Here too, each portion of the microchannel 14 is subjected to a different field strength of the magnetic field.

Figure 6:
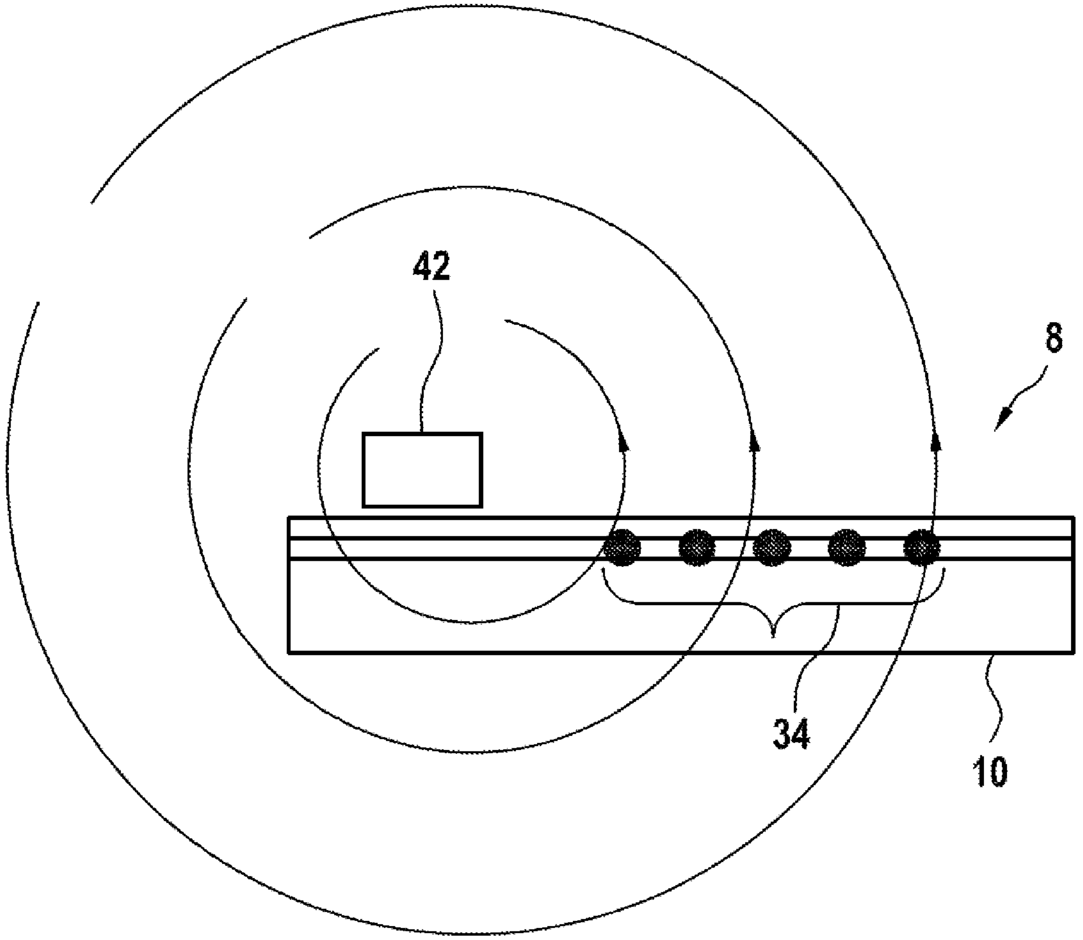
FIG. 6 a schematic illustration of a further arrangement for providing a magnetic field having a predetermined field strength profile.

FIG. 6 will now be discussed as well.

The figure shows another arrangement for providing a gradient magnetic field.

The arrangement comprises the electromagnet 42 in the form of a conductor which, in the present design example, has a rectangular cross-section and is disposed on the base body 10. The electromagnet 42 could likewise have been deposited on the base body 10 by means of additive techniques, such as galvanic deposition.

Here again, each portion of the microchannel 14 is subjected to a different field strength of the magnetic field.

Figure 7:
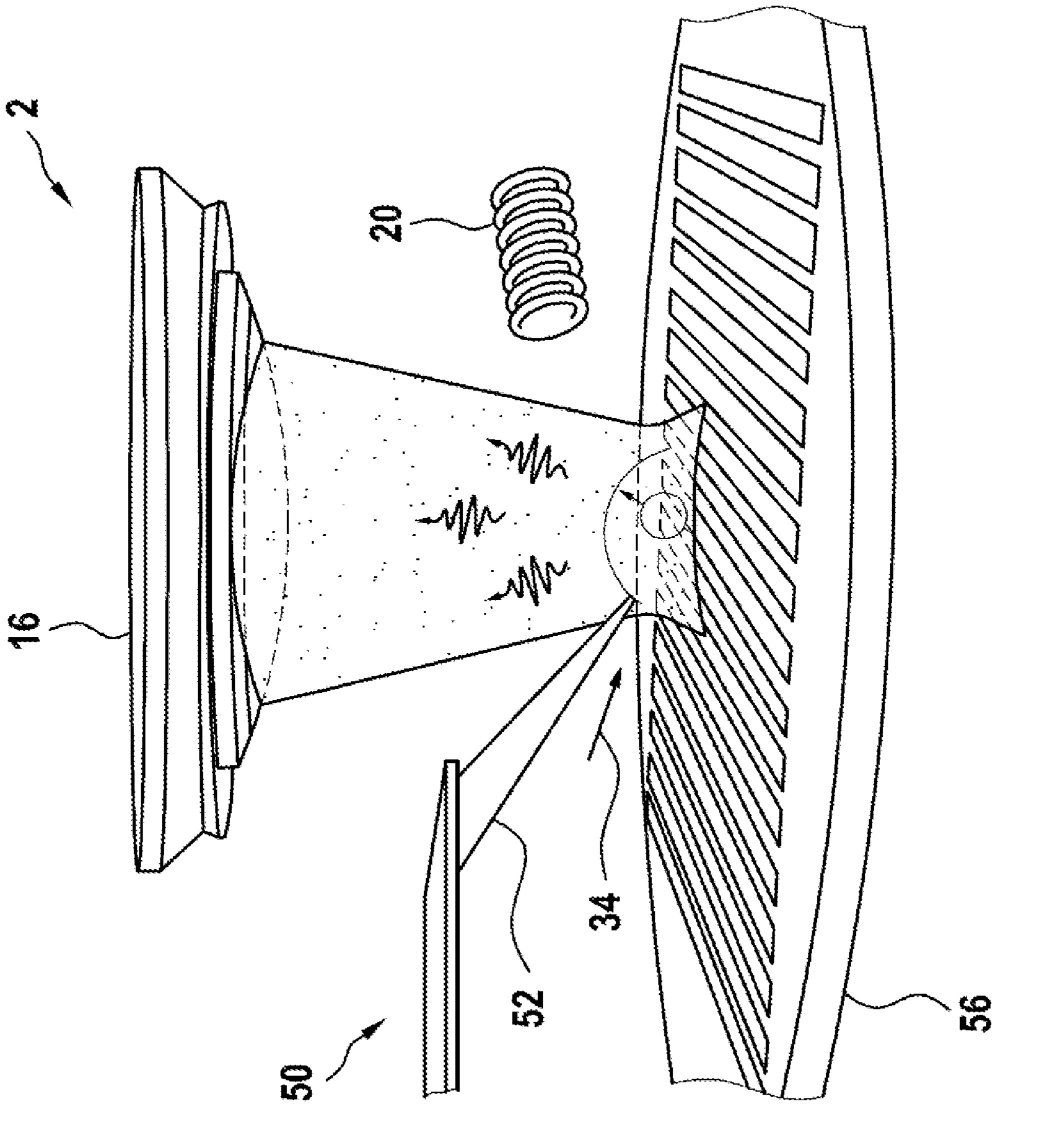
FIG. 7 a schematic illustration of components of a further system for sequencing a prepared DNA strand.

FIG. 7 will now be discussed as well.

Whereas the prepared DNA strand 4 in the previous design examples according to FIGS. 1 to 6 is shifted and the sensor unit 6 is stationary, according to the design example shown in FIG. 7, the sensor unit 6 is shifted in a predetermined manner while the prepared DNA strand 4 is stationary. It can furthermore also be provided that the prepared DNA strand 4 is shifted in a predetermined manner as well.

For this purpose, the sensor unit 6 as a whole or components of the sensor unit 6 can be disposed on a measuring tip 52 of an atomic force microscope 50. In this context, an atomic force microscope is understood to be a special scanning probe microscope for mechanically scanning surfaces and measuring atomic forces on the nanometer scale. The lateral resolution of an atomic force microscope can be accurate to 0.1 nm, which is sufficient to identify the individual nucleotides of the prepared DNA strand 4. In the present design example, the measuring tip 52 of the atomic force microscope 50 is a diamond tip comprising a single NV color center. The prepared DNA strand 4 is scanned nucleotide by nucleotide with the measuring tip 52, which is only a few nm in size, in order to identify the type of the sequentially scanned nucleotides. This is therefore a sequential identification of the types of the nucleotides. A single color center 34 is sufficient for this purpose. The prepared DNA strand 4 is fixed on a slide 56 of the atomic force microscope 50. To fix the prepared DNA strand 4, said strand can be allowed to dry on the microscope slide 56, for example. The prepared DNA strand 4 is ideally fixed in linearized form on a slide 56 having very low roughness. This can be achieved, for example, by using a microstructured glass substrate comprising microchannels as the slide 56. The prepared DNA strand 4 is then disposed in one of the microchannels of the glass substrate. Since the types of the nucleotides of the prepared DNA strand 4 are identified sequentially along the prepared DNA strand 4, the steps of identifying the types of the nucleotides of the prepared DNA strand 4 and determining their sequence are carried out in parallel.

The method for sequencing a prepared DNA strand 4 which can be carried out with the system 2 is based on the fact that, in the normal state, color centers 34, such as nitrogen-vacancy centers in a diamond in the present design example, exhibit fluorescence in the red wavelength range when optically excited. If microwave radiation is irradiated in addition to the optical excitation, there is a drop in the fluorescence at approximately 2.87 GHz because, in this case, the electrons are raised from the m=0 level of the 3A state to the m=+1 or m=−1 level of the 3A state, from which they recombine, preferably in a non-radiating manner, via the optically excited 3E state to the 3A ground state. In the presence of an external magnetic field, splitting of the m=+1 and m=−1 levels occurs (Zeeman effect) and, when the fluorescence is plotted over the frequency of the microwave excitation, two dips appear in the fluorescence spectrum, the frequency spacing of which is proportional to the magnetic field strength.

The magnetic field sensitivity is defined by the minimally resolvable frequency shift and can reach up to 1 pT/√Hz. The thus achievable high measurement accuracy and sensitivity allows the changes in the magnetic field strength caused by the magnetic labels 38 to be detected.

When nucleotides are labeled with electron spin-active atoms as the magnetic label 38, they radiate a very strong alternating magnetic field (1 nT at a distance of 40 nm), which significantly shortens the spin decoherence time of polarized NV electron spins compared to undisturbed color centers 34. This decoherence can be detected by the fact that, after optical polarization to the m=0 state, a certain part of the population is excited by the alternating magnetic field of the magnetic label 38 to the m=+1 or m=−1 state and, upon light excitation, transitions to a dark state and fluorescence is reduced in the presence of magnetic labels 38. This measurement method does not require additional microwave excitation, because the needed magnetic microwave field can be provided by the magnetic label 38. The measurement is carried out by first polarizing the electron spin of the color centers 34 via a long light pulse. It is then possible to determine the fluorescence intensity via successive light pulses and how much of the spin population has transitioned from m=0 to the m=1 state due to a magnetic label 38.

Figure 8:
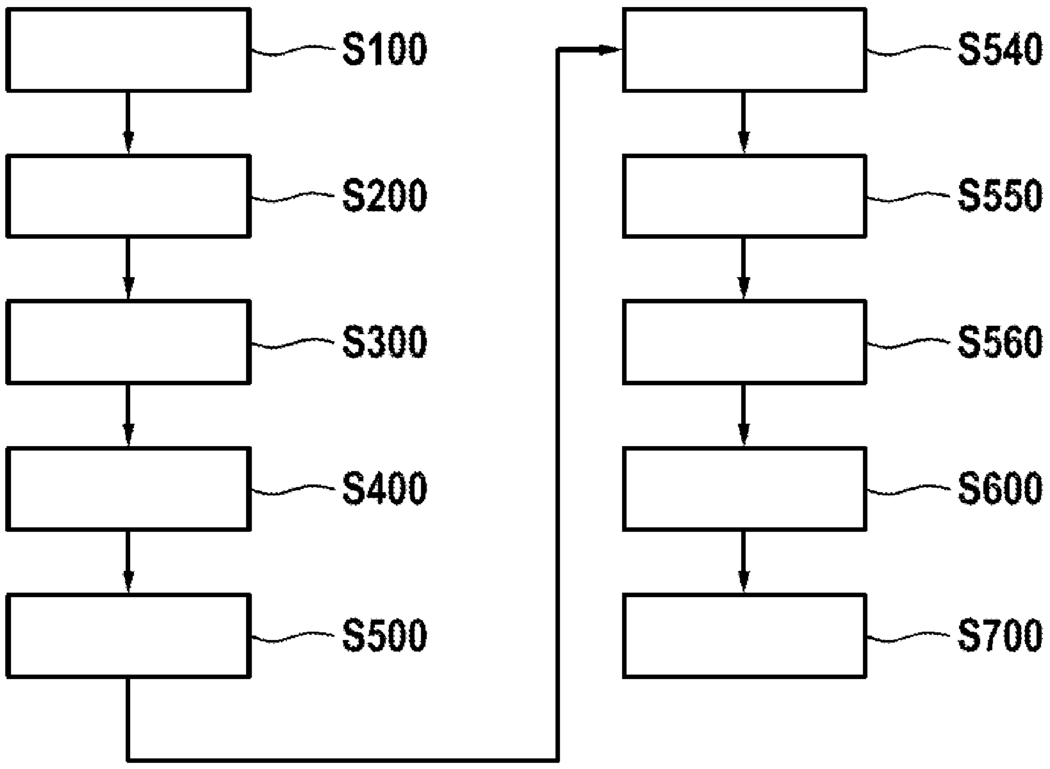
FIG. 8 a schematic illustration of a procedure for operating the systems shown in FIG. 1 or 7.

A procedure for operating the system 2 shown in FIGS. 1 and 7 will now be explained with additional reference to FIG. 8.

In the method, the sequencing of the prepared DNA strand 4 is not carried out as it is being synthesized, but after it has been synthesized. Thus, ahead of time in a first step S100, the prepared DNA strand 4 is synthesized using an original nucleic acid strand to be examined and using nucleotides of the types dATP (deoxyadenosine triphosphate), dCTP (deoxycytidine triphosphate), dGTP (deoxyguanosine triphosphate) and/or dTTP (deoxythymidine triphosphate), wherein at least one of the types of the nucleotides comprises the predetermined magnetic label 38 or can be provided with the predetermined magnetic label 38. The predetermined magnetic label 38 is specific to the type of the nucleotide. In other words, each type of magnetically labeled nucleotide comprises a different magnetic label 38 or is provided with a different magnetic label 38, so that the magnetic label 38 can be used to deduce whether the nucleotide incorporated at a particular position in the prepared DNA strand 4 is dATP, dCTP, dGTP or dTTP. Such nucleotides and their production are known.

It is therefore possible to combine a number of different magnetic labels 38 in the prepared DNA strand 4 in order to detect and distinguish the different nucleotides.

The different magnetic labels 38 can be different types of magnetic labels 38. The different types of magnetic labels 38 can be different organometallic complexes of Ni, Fe, Gd, and Mn, for example. Alternatively, the different magnetic labels 38 can be based on the same type of magnetic label 38 if it can be used in different concentration levels and the different concentration levels can be distinguished from one another.

In the present design example, the nucleotides of the types dATP, dCTP, dGTP, and dTTP are the abovementioned native forms of the nucleotides. Alternatively, it is possible to use suitable derivatives of said nucleotides, i.e., modified variants thereof, instead of one or more of the native forms of the nucleotides. Due to their modification, the derivatives of the nucleotides can exhibit other, not necessarily magneto-sensory properties. Derivatives of the nucleotides suitable for the synthesis of the prepared DNA strand 4 are known.

The original nucleic acid strand to be examined can be a DNA strand or an RNA strand.

The nucleotides used to synthesize the prepared DNA strand 4 are deoxyribonucleotides, so that the prepared strand 4 is a DNA strand.

The synthesis of the prepared DNA strand 4 derived from the original DNA strand or the original RNA strand is carried out using known molecular biological DNA synthesis methods, such as primer extension or polymerase chain reaction (PCR). The prepared DNA strand 4 can thus be a DNA strand that is complementary to the original nucleic acid strand or a DNA copy of the original nucleic acid strand. The sequence of the original nucleic acid strand can be deduced from the sequence of the prepared DNA strand 4.

In the present design example, the original nucleic acid strand is an RNA strand and the prepared DNA strand 4 is synthesized by means of primer extension. The RNA strand serves as a template and is transcribed directly into a cDNA first-strand (cDNA stands for complementary DNA) with magnetically labelled nucleotides. Thus, the cDNA first-strand already represents the prepared DNA strand 4. It is alternatively possible for the RNA strand to initially be transcribed into a cDNA first-strand with only unlabeled nucleotides and the cDNA first-strand to then serve as a template for the incorporation of the magnetically labelled nucleotides into the prepared DNA strand 4. In the present design example, all four types of the nucleotides are used and every type of nucleotide is magnetically labeled. As described above, each type of nucleotide comprises a different magnetic label 38, so that the magnetic label 38 can be used to deduce whether the nucleotide incorporated at a particular position in the prepared DNA strand 4 is dATP, dCTP, dGTP or dTTP. In the present design example, dATP comprises the organometallic complex (pyridine-2,6-diyl) bis(N-aryl-ethane-1-imine)iron dichloride as the magnetic label 38, dCTP comprises gadolinium-1,4,7,10-tetraazacyclododecane-1,4,7,10-tetraacetic acid as the magnetic label 38, dGTP comprises manganese-N-picolyl-N,N',N'-trans-1,2-cyclohexene diamine triacetic acid as the magnetic label 38 and dTTP comprises bis(cyclopentadienyl)nickel as the magnetic label 38.

Alternatively, it is possible that only one, two or three types of the nucleotides comprise the respective predetermined magnetic label 38 or can be provided with the respective predetermined magnetic label 38. For example, it is conceivable that an original nucleic acid strand known to have only two types of nucleotides complementary to one another is used. In this case, it is sufficient to use only the corresponding two types of nucleotides in the first step S100 (the two types of nucleotides can be (i) dATP and dTTP or (ii) dCTP and dGTP), whereby only one type of the nucleotides has to comprise the predetermined magnetic label 38 or has to be provided with the predetermined magnetic label 38 to fully determine the sequence of the prepared DNA strand 4. In another example, the sequence or identification of exactly two selected types of nucleotides that are not complementary to one another, for example dCTP and dTTP, is determined from a prepared DNA strand 4 in a first step, and, in a second step, the sequence or identification of the same two types of nucleotides is determined, but on the basis of the prepared opposite strand of the prepared DNA strand 4 used in the first step. Due to the complementary base pairing between the prepared DNA strand 4 and its opposite strand, specifically the two types of nucleotides not yet identified in the first step (for example dATP and dGTP) of the prepared DNA strand 4 are identified by means of the second step, because the complementary types of nucleotides are localized on the opposite strand used in the second step. The sequence of the prepared DNA strand 4 is thus fully determined using two prepared strands, namely the prepared DNA strand 4 itself and the prepared opposite strand to the prepared DNA strand 4, by appropriate overlapping of the signals. In that case, it is sufficient if only the two selected types of nucleotides that are not complementary to one another, for example dCTP and dTTP, comprise the respective predetermined magnetic label 38 or can be provided with the respective predetermined magnetic label 38.

In the present design example, the nucleotides comprise the magnetic label 38 on the base. Alternatively, it is possible for the nucleotides to be provided with the magnetic label 38 on the base. In a further alternative, it is possible for the nucleotides to comprise the magnetic label 38 on the pentose or be provided with the magnetic label 38 on the pentose. The magnetic label 38 is retained when the nucleotides are incorporated into the prepared DNA strand 4. Nucleotides, the magnetic label 38 of which is attached to a terminal phosphate of the nucleotides, are therefore not suitable.

When using nucleotides comprising the magnetic label 38, the magnetic label 38 is incorporated directly into the prepared DNA strand 4 during the synthesis thereof. The magnetic label 38 is an organometallic complex of Ni(II), for example. Other examples of nucleotides that comprise a magnetic label 38 are isotopically labeled nucleotides.

The use of nucleotides that can be provided with the magnetic label 38, on the other hand, results in a two-step approach. In the two-step approach, the nucleotides are incorporated into the DNA strand in a first step during the synthesis thereof and provided with the magnetic label 38 in a subsequent second step, as a result of which the prepared DNA strand 4 is obtained. The magnetic label 38 is an organometallic complex of Ni(II), for example, and the nucleotide incorporated in the prepared DNA strand 4 is provided with the magnetic label 38 by means of a click reaction.

A nucleotide that can be provided with a magnetic label 38 can be provided with a chemical "handle," for example, to which the magnetic label 38 is attached in the second step. The most important requirements for this strategy are that the selected chemical handle is orthogonal to all other reactive groups in the prepared DNA strand 4, is compatible with aqueous solution and is quantitative. The so-called click chemistry or click reaction satisfies these requirements. In addition to very high yields, click chemistry also offers a high degree of selectivity and simple implementation. The click reaction can be a reaction between an organic azide and a terminal alkyne which leads to a covalent product (1,4-disubstituted 1,2,3-triazole) and is typically catalyzed by copper(I) (copper(I)-catalyzed azide-alkyne cycloaddition). Since copper ions can lead to strand breaks, ligands such as tris[(1-benzyl-1H-1,2,3-triazol-4-yl)methyl]amine (TBTA) which chelate copper(I) are typically used and thereby prevent any strand breaks. For a copper-free click reaction, sterically loaded alkynes can be reacted with organic azides or trans-cyclooctene can be coupled with tetrazine (third generation click chemistry). A nucleotide provided with either an alkyne handle, a trans-cyclooctene handle, an azide handle or a tetrazine handle can therefore be incorporated into the DNA strand 4 in the first step. In the subsequent second step, the nucleotide is provided with the magnetic label 38 by means of a click reaction, for which purpose the magnetic label 38 is provided with the corresponding other reactive group. The reactive group can be connected to the magnetic label 38 via a linker (also referred to as a spacer), for example. The linker can be a carbon chain, for example, an ethylene glycol chain, or a polyethylene glycol (PEG) chain.

The magnetic label 38 is well-suited to generate a magnetically detectable signal on the magneto-optical transducer unit 8. The signal can be generated directly or, for example, as a result of hyperpolarization.

One group of suitable magnetic labels 38 are paramagnetic organometallic complexes of Ni(II), Fe(III), Gd(III) and Mn(II). Examples of suitable chelators for the organometallic complexes are DOTA (1,4,7,10-tetraazacyclododecane-1,4,7,10-tetraacetic acid), DTPA (diethylenetriaminepentaacetic acid), DO3A (1,4,7,10-tetraazacyclododecane-1,4,7-triacetic acid), AAZTA (6-amino-6-methylperhydro-1,4-diazepinetetraacetic acid), DPDP (dipyridoxyl diphosphate) and PyC3A (N-picolyl-N,N',N'-trans-1,2-cyclohexene diamine triacetic acid). Examples of the organometallic complexes include the complexes bis(cyclopentadienyl)nickel, (pyridine-2,6-diyl)bis(N-aryl-ethane-1-imine)iron dichloride, gadolinium-1,4,7,10-tetraazacyclododecane-1,4,7,10-tetraacetic acid and manganese-N-picolyl-N,N',N'-trans-1,2-cyclohexene diamine triacetic acid used in the present design example.

The organometallic complexes of Ni(II), Fe(III), Gd(III), and Mn(II) can be chemically modified for use as magnetic labels 38 for nucleotides for sequencing by introducing a functional group for binding to the nucleotide by means of a click reaction or other suitable reaction.

Figure 9:
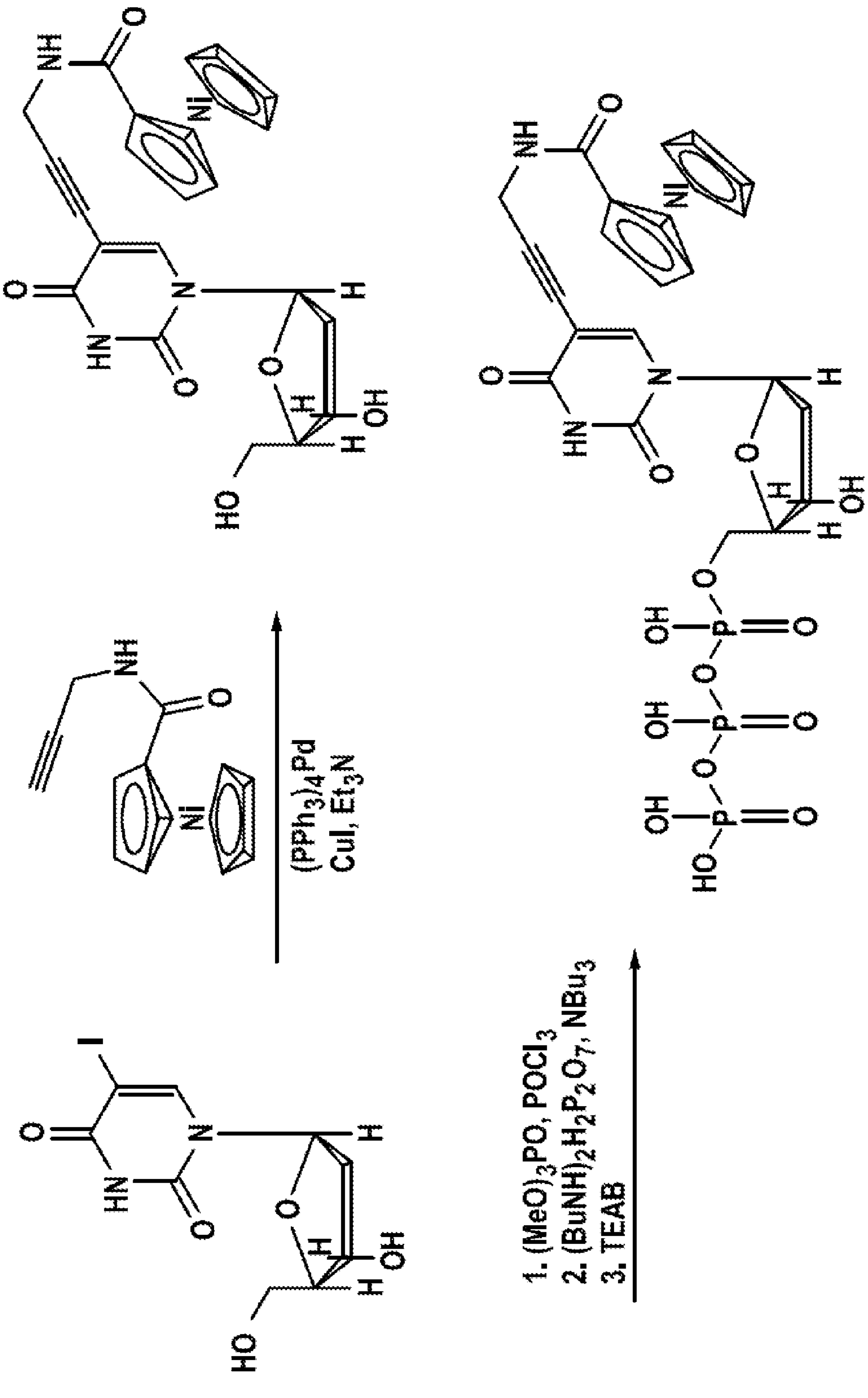
FIG. 9 a synthesis pathway for producing a nucleotide comprising a predetermined magnetic label.

FIG. 9 shows an example of synthesis pathway for producing a nucleotide comprising an organometallic complex of Ni(II) as a magnetic label 38 on the base. The nucleotide shown as an example is a nucleotide of the type dTTP.

Another group of suitable magnetic labels 38 are isotopes such as D (deuterium, $^{2}H$), $^{13}C$, $^{18}O$ and $^{15}N$. Stable isotopes can be introduced into the nucleotides by means of chemical synthesis or enzyme-mediated exchange.

Atoms exhibiting non-vanishing nuclear spin can also be considered as suitable magnetic labels 38, in particular those atoms that have a different gyromagnetic ratio than hydrogen $^{1}H$ Examples of such atoms are $^{7}Li$, $^{14}N$, $^{15}N$, $^{17}O$, $^{19}F$, $^{23}Na$, $^{27}Al$, $^{29}Si$, $^{31}P$, $^{57}Fe$, $^{63}Cu$ and $^{67}Zn$.

In a further step S200, the prepared DNA strand 4 is provided with the magnetic labels 38.

In a further step S300, the prepared DNA strand 4 is placed within the measuring range of the sensor unit 6 comprising the magneto-optical transducer unit 8 and the optical sensor 16.

In a further step S400, the magneto-optical transducer unit 8 is optically excited. The light source 18, for example, is used for this purpose.

In a further step S500, the magneto-optical transducer unit 8 is subjected to microwave radiation. The microwave and RF source 20 is used for this purpose, for example.

In a further step S540, a spin polarization is carried out.

Since the nuclear spins in this case are only statistically polarized, the magnetic field signal is very weak and is based only on a statistically present and fluctuating unequal distribution of the nuclear spin polarizations (signals from spin-up and spin-down nuclear spins cancel each other out; a resulting magnetization stems only from a very small statistical unequal distribution of the nuclear spin orientations).

To further increase the signal strength of the nuclear spin signals at the color centers 34, the nuclear spins are polarized. This increases the resulting magnetic field of the precessing nuclear spins, because there is then an effective magnetization of all involved nuclear spins in one and the same direction. This can be achieved either by extremely strong magnetic fields applied to the color centers 34 or by polarization via the electron spins of the color centers 34.

The polarization of the nuclear spins via the electron spin of the color centers 34 can be accomplished via a targeted excitation of hyperfine transitions of the electron spins. To this end, after an optical light pulse for electron spin polarization, initially only a single hyperfine transition is excited over a precisely defined microwave frequency. A final RF-pi pulse, the frequency of which corresponds to the hyperfine splitting between m=+1 and m=−1, polarizes the nuclear spin into the respectively addressed state.

In a further step S550, the magneto-optical transducer unit 8 is subjected to a static magnetic field and, in a further step S560, the magneto-optical transducer unit 8 is subjected to an RF (radio frequency) magnetic field.

The DC solenoid 22 with DC magnetic field source 24 can be used to apply a static magnetic field, for example, while microwave and RF source 20 can be used to apply RF, for example.

The static magnetic field leads to a precession of the nuclear spins of the magnetic labels 38, defined via the gyromagnetic ratio. This precession, which captures all of the nuclear spins in the sample, acts like an alternating magnetic field that leads to a periodic frequency shift of the magnetic resonance. Since all of the nuclear spins initially precess with the same frequency, but with different phases, they are excited to in-phase (coherent) movement via an additional RF magnetic field (drive field), which creates a detectable magnetic field.

If there are magnetic labels 38 in the vicinity of the color centers 34, there is a frequency component in the acquired magnetic field signature that corresponds exactly to the expected Larmor frequency characteristic of the particular nuclear spin species to be analyzed. To specifically filter out this frequency, pulsed measurement methods such as the MRXV8 or XY8 pulse schema, for example, can be used.

Common to these pulse schemas is that π-pulses are always applied to the color center 34 after polarization by a first optical pulse, and the time interval between the pulses correlates with the Larmor frequency ($\omega_L/2\pi=1/2\tau$). If the fluorescence intensity is weakened after a final π/2 pulse and subsequent laser pulse excitation, one or more nuclear spins having the characteristic Larmor frequency are present in the vicinity of the color center 34.

In a further step S600, at least one value indicative of a fluorescence signal of the magneto-optical transducer unit 8 is acquired. The optical sensor 16 is used for this purpose, for example.

In a further step S700, the acquired value is assigned to the at least one type of the nucleotides comprising the predetermined magnetic label 38.

Deviating from the present design example, it is also possible for the order of steps to be different. Multiple steps can furthermore also be carried out at the same time or simultaneously. Moreover, likewise deviating from the present design example, individual steps can also be skipped or omitted.

Thus, by using a magneto-optical transducer unit 8, a method can be provided that has sufficient measurement accuracy to detect the changes in the magnetic field strength caused by the magnetic labels 38 in a spatially resolved manner and thus enable sequencing of a prepared DNA strand 4.

The invention claimed is:

1. A method of sequencing a prepared DNA strand, comprising:

providing the prepared DNA strand with nucleotides of the types dATP, dCTP, dGTP and/or dTTP, wherein at least one of the types of the nucleotides comprises a predetermined magnetic label;

placing the prepared DNA strand within a measuring range of a sensor unit comprising an operatively connected magneto-optical transducer unit and an optical sensor;

optically exciting the magneto-optical transducer unit;

acquiring at least one value indicative of a fluorescence signal of the magneto-optical transducer unit; and assigning the acquired value to the at least one type of the nucleotides comprising the predetermined magnetic label.

2. The method according to claim 1, further comprising: subjecting the magneto-optical transducer unit to microwave radiation.

3. The method according to claim 1, further comprising: subjecting the magneto-optical transducer unit to a static magnetic field; and subjecting the magneto-optical transducer unit to an RF magnetic field.

4. The method according to claim 3, wherein a gradient magnetic field is used as the static magnetic field.

5. The method according to claim 1, further comprising: carrying out a spin polarization.

6. The method according to claim 1, wherein:

the sensor unit is stationary and the prepared DNA strand is shifted in a predetermined manner;

the prepared DNA strand is stationary and the sensor unit is shifted in a predetermined manner relative to the prepared DNA strand; or the prepared DNA strand and the sensor unit are both shifted in a predetermined manner.

7. A computer program product comprising at least one non-transitory computer-readable storage medium having computer-executable program code portions stored therein, the computer-executable program code portions comprising program code instructions configured to:

place a prepared DNA strand with nucleotides of the types dATP, dCTP, dGTP and/or dTTP, wherein at least one of the types of the nucleotides comprises a predetermined magnetic label, within a measuring range of a sensor unit comprising an operatively connected magneto-optical transducer unit and an optical sensor;

optically excite the magneto-optical transducer unit;

acquire at least one value indicative of a fluorescence signal of the magneto-optical transducer unit; and assign the acquired value to the at least one type of the nucleotides comprising the predetermined magnetic label.

8. A system for sequencing a prepared DNA strand, wherein the prepared DNA strand comprises nucleotides of the types dATP, dCTP, dGTP and/or dTTP, wherein at least one of the types of the nucleotides comprises a predetermined magnetic label, comprising:

a sensor unit comprising an operatively connected magneto-optical transducer unit and an optical sensor, with a light source configured to optically excite the magneto-optical transducer unit, wherein the optical sensor is configured to acquire at least one value indicative of a fluorescence signal of the magneto-optical transducer unit, and the system is configured to assign the acquired at least one value to the at least one type of nucleotide comprising the predetermined magnetic label.

9. The system according to claim 8, wherein the system further comprises:

a microwave source configured to apply microwave radiation to the magneto-optical transducer unit.

10. The system according to claim 8, further comprising:

a magnet configured to apply a static magnetic field to the magneto-optical transducer unit; and a microwave source configured to apply an RF magnetic field to the magneto-optical transducer unit.

11. The system according to claim 10, wherein the magnet is configured to provide a gradient magnetic field as the static magnetic field.

12. The system according to claim 8, wherein the system is further configured to carry out a spin polarization.

13. The system according to claim 8, wherein the system is configured to:

shift the prepared DNA strand in a predetermined manner while maintaining the sensor unit stationary;

shift the sensor unit relative to the prepared DNA strand in a predetermined manner while maintaining the prepared DNA strand stationary; or shift both the prepared DNA strand and the sensor unit in a predetermined manner.

* * * * *